US010520449B2

United States Patent
Piana

(10) Patent No.: US 10,520,449 B2
(45) Date of Patent: Dec. 31, 2019

(54) INSPECTION METHOD AND INSPECTION DEVICE FOR THE CLOSURE CONTROL OF CONTAINERS

(71) Applicant: KRONES AG, Neutraubling (DE)

(72) Inventor: Stefan Piana, Koefering (DE)

(73) Assignee: KRONES AG, Neutraubling (DE)

(*) Notice: Subject to any disclaimer, the term of this patent is extended or adjusted under 35 U.S.C. 154(b) by 78 days.

(21) Appl. No.: 15/737,238

(22) PCT Filed: May 23, 2016

(86) PCT No.: PCT/EP2016/061535
§ 371 (c)(1),
(2) Date: Dec. 15, 2017

(87) PCT Pub. No.: WO2016/202528
PCT Pub. Date: Dec. 22, 2016

(65) Prior Publication Data
US 2018/0172603 A1    Jun. 21, 2018

(30) Foreign Application Priority Data
Jun. 19, 2015  (DE) .................... 10 2015 211 317

(51) Int. Cl.
*G01N 21/90* (2006.01)
*G01M 3/22* (2006.01)
(Continued)

(52) U.S. Cl.
CPC ....... *G01N 21/9054* (2013.01); *G01B 11/167* (2013.01); *G01B 11/24* (2013.01);
(Continued)

(58) Field of Classification Search
CPC ....... G01B 11/167; G01B 11/24; G01B 11/25; G01B 11/2518; G01B 11/2531;
(Continued)

(56) References Cited

U.S. PATENT DOCUMENTS 4,907,443 A    3/1990  Pailler
4,914,289 A *  4/1990  Nguyen ............. G01N 21/8806
                                              250/223 B
(Continued)

FOREIGN PATENT DOCUMENTS

AT    5 10 294 A4     3/2012
DE    195 40 545 A1   5/1997
(Continued)

OTHER PUBLICATIONS

International Search Report and Written Opinion dated Dec. 22, 2016, on Application No. PCT/EP2016/061535, 10 pgs.

*Primary Examiner* — Gordon J Stock, Jr.
(74) *Attorney, Agent, or Firm* — Lowenstein Sandler LLP

(57) ABSTRACT

Implementations disclose methods and devices for closure control of containers. A method includes performing, by an inspection apparatus, optical 3D measuring of a closed container, the closed container comprising a closure coupled to the container; generating, by the inspection apparatus, 3D data based on the optical 3D measuring; and processing, by an evaluation device, the 3D data to determine at least one of tightness or correct seating of the closure relative to the container.

20 Claims, 3 Drawing Sheets

(51) Int. Cl.
*G01M 3/36* (2006.01)
*G01M 3/38* (2006.01)
*G01B 11/16* (2006.01)
*G01B 11/24* (2006.01)

(52) U.S. Cl.
CPC ............. *G01M 3/226* (2013.01); *G01M 3/36* (2013.01); *G01M 3/38* (2013.01); *G01N 21/909* (2013.01); *G01N 21/9009* (2013.01); *G01N 2201/061* (2013.01); *G01N 2201/0635* (2013.01)

(58) Field of Classification Search
CPC .............. G01B 11/2436; G01B 11/254; G01B 11/2545; G01B 11/30; G01B 11/303; G01B 11/306; G01M 3/226; G01M 3/227; G01M 3/36; G01M 3/363; G01M 3/366; G01M 3/38; G01N 21/88; G01N 21/8803; G01N 21/8806; G01N 21/8851; G01N 21/9054; G01N 21/9081; G01N 21/909; G01N 21/958; G01N 2021/8812; G01N 2021/8816; G01N 2021/8822; G01N 2021/8825; G01N 2021/8829; G01N 2021/8832; G01N 2021/8835; G01N 2021/8887; G01N 2021/889; G01N 2021/8893; G01N 2201/061; G01N 2201/0635
See application file for complete search history.

(56) References Cited

U.S. PATENT DOCUMENTS

| | | | | |
|---|---|---|---|---|
| 5,072,127 A | * | 12/1991 | Cochran | G01N 21/8806 250/223 B |
| 5,136,157 A | * | 8/1992 | Apter | G01N 21/90 250/223 B |
| 5,369,713 A | | 11/1994 | Schwartz et al. | |
| 6,072,575 A | * | 6/2000 | Loll | G01N 21/9054 356/239.1 |
| 6,784,447 B2 | * | 8/2004 | Gochar, Jr. | G01N 21/95 250/223 R |
| 7,982,868 B2 | * | 7/2011 | Akkerman | B07C 5/3404 356/240.1 |
| 8,179,434 B2 | * | 5/2012 | Koval | G01B 11/245 348/352 |
| 9,417,145 B2 | * | 8/2016 | Cochran | G01L 5/24 |
| 9,649,856 B2 | | 5/2017 | Lindner et al. | |
| 9,797,710 B2 | * | 10/2017 | Falkenstein | G01B 11/02 |
| 9,927,372 B2 | * | 3/2018 | Niemela | G01N 21/95 |
| 10,184,900 B2 | * | 1/2019 | Leconte | G01N 21/9054 |
| 10,323,933 B2 | * | 6/2019 | Fujiwara | G06T 7/521 |
| 2010/0259746 A1 | | 10/2010 | Ohnishi et al. | |
| 2012/0304763 A1 | | 12/2012 | Troxler | |
| 2019/0226999 A1 | * | 7/2019 | Hudson | G01B 11/28 |

FOREIGN PATENT DOCUMENTS

| | | |
|---|---|---|
| DE | 10 2008 023047 A1 | 11/2009 |
| DE | 10 2012 209305 A1 | 12/2013 |
| GB | 1 469 240 A | 4/1977 |
| GB | 2 204 125 A | 11/1988 |
| JP | H09-169392 A | 6/1997 |
| JP | 2009128261 A * | 6/2009 |
| JP | 5 499 289 B1 | 5/2014 |
| JP | 2015102360 A * | 6/2015 |

* cited by examiner

INSPECTION METHOD AND INSPECTION DEVICE FOR THE CLOSURE CONTROL OF CONTAINERS

This application claims the benefit of International Application No. PCT/EP2016/061535, filed May 23, 2016, that claims priority to German Application No. 102015211317.5, filed Jun. 19, 2015, the entire contents of both are hereby incorporated by reference.

The present disclosure relates to an inspection method for closure control of containers and an inspection device In inspection methods for closure control of containers, the closed containers are typically transported by a transport apparatus and inspected with an inspection device in terms of tightness and/or correct seating of closures applied to the containers.

For example, in a known method, the crown cap is made to vibrate by way of an electromagnetic pulse and conclusions about an incorrectly seated crown cap are drawn from the vibration behavior. However, this method is only suitable for metal closures.

Methods in which a closure logo is captured from above using a camera or the closure together with the container neck from a lateral view are likewise known. Mirror cabinets with high-resolution cameras are also employed to simultaneously capture the closed container on a camera image from multiple directions of view. The images captured with the camera are then evaluated by way of image processing for correct seating of the closure. To perform reliable closure control, however, a plurality of directions of view must be captured and evaluated, which is respectively complex.

An inspection method is also known in which the curvature of the closure is measured by way of an optical distance sensor or a magnetic proximity sensor and the internal pressure is concluded therefrom. It is there particularly disadvantageous that the final pressure in the container is reached only after 20-30 minutes, typically after pasteurization, and reliable measurement can be performed only then.

Consequently, different methods have to be used in order to perform reliable closure control, depending on the various container and closure types. Furthermore, several cameras and views are possibly necessary for the imaging methods to ensure reliable closure control. This requires a correspondingly high effort in terms of costs, installation space and equipment.

The object of the present disclosure is therefore to provide an inspection method and an inspection device for closure control of containers with which reliable closure control of a wide variety of container and closure types is possible and which is of a particularly simple configuration in terms of the use of inspection hardware.

To satisfy this object, the present disclosure provides an inspection method for closure control of containers.

Advantageous developments are mentioned in the present disclosure.

By using an optical 3D measuring method in the inspection method, the surface of the container or the respective closure applied thereto is captured spatially with particularly high resolution, accurately and without contact. With the high-resolution measurement of surface data of the container together with its closure and the 3D data generated therefrom, the evaluation device is provided with a comprehensive amount of information, without depending on the direction of view of the camera, where the evaluation of the 3D data after being captured can be customized to the various types of containers or types of closures. In other words, the inspection method no longer requires changing the measuring method, but merely an evaluation that is customized to the container or the closure, respectively, for example, by way of appropriate software parameterization.

The inspection method can be performed in a beverage processing system, for example, in an inspection device. For example, the inspection method can be used in a full bottle inspection machine. The inspection method can be performed after the containers are filled and closed, for example, downstream of a filler and a capper. It is likewise conceivable that the inspection method is performed with closed containers that are already grouped in a packaging unit.

The containers can be provided to receive beverages, foods, hygiene products, pastes, chemical and biological and/or pharmaceutical products. The containers can be, in particular, plastic bottles, glass bottles, cans, and/or tubes. Plastic containers can be, in particular, PET, PEN, HD-PE or PP containers or bottles, respectively. They can also be biodegradable containers or bottles, the main components of which are made of renewable raw materials such as sugar cane, wheat or corn. The closure can be a crown cap, screw cap, tear-off closure or the like.

The optical 3D measuring method can be adapted to capture a face end and/or at least in part an edge of the closure and/or at least in part the container neck. The container together with its closure can be captured with the optical 3D measuring method from one or more directions of view. It is conceivable that the 3D data from several directions of view are matched together. It is also conceivable that the container is rotated by a container holder for capturing a plurality of directions of view. Alternatively, a container can be captured with the optical 3D measuring method simultaneously from several directions of view, for example, by way of several optical 3D measuring sensors.

The 3D data can be 3D points, 3D line elements and/or 3D area elements. The 3D points can be surface points of the container and the closure in a three-dimensional or spatial coordinate system. The 3D line elements can be straight lines, curves such as circle segments and/or splines. The 3D area elements can be triangles and/or rectangles, which are preferably connected in one or more surface grids.

The evaluation device can be a computer, a machine control unit or separate image processing hardware, which in particular comprise a CPU, a memory and/or a data interface. The evaluation device can be arranged separately or integrated at least in part in a 3D measuring sensor. The evaluation device can be configured to evaluate the 3D data geometrically, in order to obtain conclusions from this regarding the tightness and/or the correct seating of the closure. The evaluation device can be connected via a data bus or the like to a discharge device to discharge containers with a leaky or incorrectly applied closure, for example, by way of a controllable track switch. Faulty containers can be forwarded, for example, to a recycling system to recover their material.

The 3D data of the closure and the 3D data of the container can be separated from one another when processed by the evaluation device. In other words, it is conceivable that the 3D data is respectively assigned to the closure and the container, respectively. This makes it possible to supply the 3D data of the closure or of the container, respectively, to different evaluation methods. For example, geometric correlation features between the closure and the container can be determined when processing the 3D data. Geometrical correlation features can mean how the closure is positioned relative to the container. For example, when processing 3D data, a position, a height, a crooked seat and/or an eccentricity of the closure relative to the container can be determined. A position can presently mean how a reference coordinate system of the closure is disposed relative to a reference coordinate system of the container. It can also mean at which position or with which orientation the closure is located in a container coordinate system. The height of the closure can presently mean at which position along a container longitudinal axis the closure is located. A crooked seat can mean, e.g. the tilt angle between the plane of the support ring or the mouth surface of the container relative to the bearing plane or the upper boundary plane of the approximately cylindrical closure. Eccentricity of the closure can mean the distance of a center of the closure to a container longitudinal axis.

Furthermore, a curvature of the closure can be determined when processing the 3D data. The curvature of the closure can mean buckling of the closure due to the internal pressure prevailing in the container. In order to determine the curvature, it is conceivable that a surface, which can be parameterized with regard to its curvature, is fitted by the 3D data of the face side of the closure. A conclusion about the curvature of the closure can then be drawn from the curvature of the parameterizable surface.

During processing, the 3D data can at least in part be compared with reference geometry and, in particular, deformation data of the closure can be determined therefrom. It is conceivable that CAD data originating from the construction of the container or the closure serves as reference geometry. It is also conceivable that the reference geometry is available as 3D points, 3D line elements and/or 3D area elements within the meaning of the 3D data described above. For example, the smallest distance to the reference geometry can be determined for the 3D data, for example, to a corresponding 3D point or a corresponding 3D area of the reference geometry. The deformation data of the closure can, in particular, comprise the curvature of the closure. A conclusion regarding the internal pressure prevailing in the container and thus regarding the tightness can be drawn from the deformation data or the curvature of the closure. If, for example, the curvature of the closure is too low with respect to a reference value, then it is possible to conclude that the internal pressure is too low and that a leak therefore exists.

The 3D measuring method can comprise a stereoscopic 3D measuring method in which the container together with its closure are at least in part captured from two image perspectives. The stereoscopic 3D measuring method therefore means that the surface points on the container or on the closure, respectively, are each captured from the two image perspectives and that their coordinates in a coordinate system are calculated therefrom. If, for example, two cameras are used in the stereoscopic 3D measuring method, which at least in part capture the container together with its closure from different directions, then the same surface point on the container or on the closure is respectively identified in both camera images. Subsequently, the position of the object point is calculated (triangulated) by way of the corresponding pixel coordinates in the two camera images and by way of the arrangement of the two cameras in space and by way of imaging parameters of the objective lenses.

With the stereoscopic 3D measuring method, it is also conceivable that the container together with its closure is at least in part captured by a camera with a stereoscopic objective lens, where the stereoscopic objective lens images two or more image perspectives on a single image sensor of the camera.

In the stereoscopic 3D measuring method, the container together with its closure can be at least in part illuminated by a diffuse light source. This results in particularly uniform illumination of the container and the closure, so that the contrast in the optical recording is particularly uniform. For example, both diffuse and highly specularly reflective closures and container surfaces can then be captured well with the optical 3D measuring method.

With the stereoscopic 3D measuring method, the container with its closure can at least in part be illuminated by a structured light source for the correlation of the same object points in the two image perspectives. As a result, a particularly simple correlation of the same object points in the two image perspectives is possible since they can be reliably identified with a particularly low computation effort due to the structure applied by the light source. Moreover, this can increase the accuracy of the stereoscopic 3D measurement method. The structured light source can, for example, project regular or stochastically distributed light points. It is also conceivable that the structured light source projects a regular or irregular pattern, such as a grid or stripes.

Alternatively, the 3D measuring method can also comprise a light-section 3D measuring method in which the container is illuminated together with its closure at least in part from a first direction by way of a structured light source and is captured by a camera from a second direction that is angled thereto. As a result, only one camera needs to be employed and the structured light source serves as an inverse camera. Consequently, the 3D measurement is obtained very reliably and with low equipment complexity. The structured light source can be coded in such a way that light planes of the light source can be unambiguously identified in the camera image. For example, the structured light source can be coded with a gray code method or the like. It is also conceivable that the structured light source is coded spatially or temporally, where different light patterns are successively projected onto the container or the closure in the temporal coding. With the light-section 3D measuring method, it is also conceivable that only one light plane is projected, for example, by use of a laser line, and that it is captured with a camera. As a result, the line can be captured particularly easily in the camera and object points on the line can be determined particularly easily. It is further possible to generate planar 3D data by way of a relative motion of the closed container substantially transverse to the light line of the 3D measuring sensor. It is conceivable that the container is transported by the transport apparatus for this purpose and then moved relative to the 3D measuring sensor. It is also conceivable that this is done following a dedicated trajectory.

In the 3D measuring method, the container together with its closure is preferably captured at least in part in three dimensions with a resolution of <0.5 mm, preferably <0.2 mm or more preferably <0.1 mm. The resolution presently means, for example, the lateral distance of the 3D points relative to each other. The resolution can correspond to the image sensor raster of the camera of the 3D measuring sensor. The lower the resolution, i.e. the smaller the spacing of the 3D data obtained, the more accurately local features of the closure or of the container can be captured. This allows for even more reliable closure control. Due to the large number of contour points captured, the 3D points could also be calculated at a higher resolution as compared to the image sensor raster.

In the inspection method, it is further conceivable that the closure and/or a mouth of the container are captured at least in part by a pericentric objective lens. Pericentric can presently mean that the beam path of the objective lens does not diverge on the side of the container or the closure but converges. This makes it possible for the objective lens to monitor the closure, in particular its edge, simultaneously from several directions. The front lens of the pericentric objective lens can preferably be larger than the closure of the container. This makes it possible to capture the closure or the mouth of the container from above or at the edge, respectively, as completely as possible in one camera image.

In addition, the present disclosure provides an inspection device for closure control of containers. Advantageous developments are mentioned in the present disclosure.

Due to the fact that the inspection device comprises the optical 3D measuring sensor, the container with its closure can be captured three-dimensionally and high-resolution 3D data can be obtained. The evaluation of the 3D data can then be performed according to the inspection method described above, so that the same inspection device can be used regardless of the type of container or closure. Consequently, only the evaluation of the 3D data generated must be customized by suitable parameterization. In addition, the 3D data of the optical 3D measuring sensor is particularly accurate, whereby, for example, the deformation of the closure and its position relative to the container can be incorporated in the closure control. Consequently, reliable closure control of a variety of container or closure types is possible with inspection hardware of a particularly simple design.

The inspection device can be arranged in a beverage processing system. The inspection device can be arranged downstream of a filler and a capper for the closed containers.

The transport apparatus can comprise a carousel or a linear conveyor device. In addition, the transport apparatus can comprise container holders for the closed containers. It is conceivable that the container holders are configured to rotate the container about their longitudinal axis and/or to tilt them relative to the 3D measuring sensor. It is therefore conceivable that the container holders are adapted to pivot the container about one or more axes. As a result, the container or the closure, respectively, can be captured by the optical 3D measuring sensor from several perspectives.

The optical 3D measuring sensor can be configured for a stereoscopic 3D measuring method and for this purpose comprise a camera with a stereoscopic objective lens or two or more cameras each with an objective lens, and furthermore preferably be equipped with a diffused or structured light source. Due to the fact that the optical 3D measuring sensor is configured for the stereoscopic 3D measuring method, the container with its closure can be captured without contact and particularly accurately with high resolution and 3D data can be generated therefrom. For example, the 3D data is calculated by triangulating the image data. The one camera with the stereoscopic objective lens or the two or more cameras can capture camera images from at least two different image perspectives. With two different image perspectives presently means at least two directions of view of the cameras that run diagonally to each other.

The optical 3D measuring sensor can be configured for a light-section 3D measuring method and for this purpose comprise at least one camera with an objective lens and a structured light source. As a result, only one camera is necessary for capturing the 3D data, and the equipment complexity of the optical 3D measuring sensor is particularly low. The structured light source can comprise a projector for projecting a pattern, which is preferably configured to project different patterns, for example, by way of a movable grid, an LCD, an LCoS, a DMD or the like. The structured light source can also comprise a laser as well as upstream optics for generating a line. The optics can be, for example, a diffractive grid. It is also conceivable that a grid or a pattern of dots is projected with the laser.

The objective lens(es) of the camera can be pericentric. As a result, the closure or the container mouth, respectively, can be captured around the container longitudinal axis with one camera image.

In addition, the inspection device can comprise one or more of the features previously described with respect to the inspection method in any combination.

Further features and advantages shall be explained below with reference to embodiments illustrated in the figures, where FIG. 1 shows an embodiment of the inspection method for closure control of containers as a flow chart;

Figure 1:
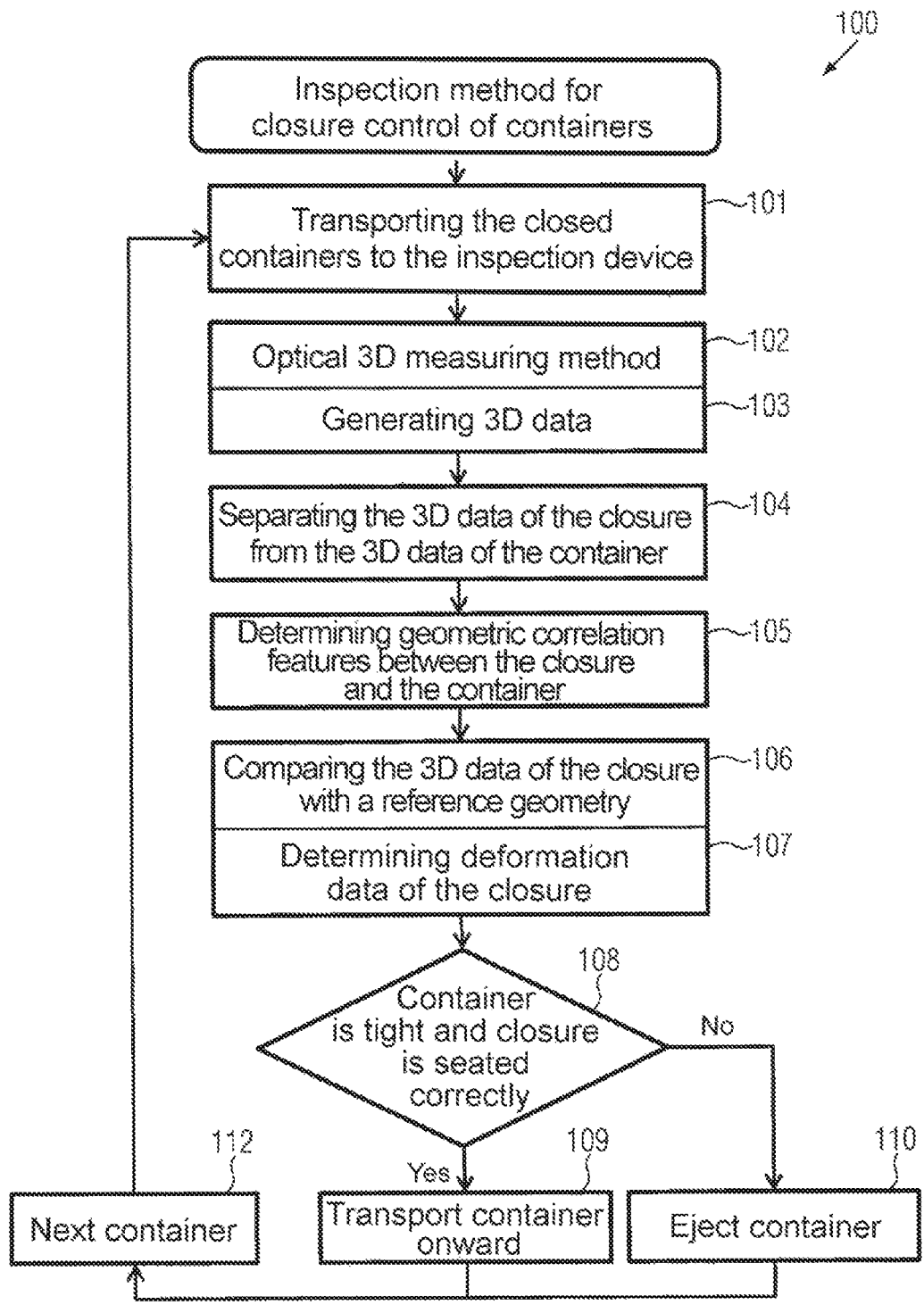
FIG. 1 shows an embodiment of inspection method 100 for closure control of containers in a flow chart. Individual method steps 101-112 described below are shown.

First, in step 101, a closed container is transported to the inspection device and inspected with subsequent method steps 102-112 with regard to tightness and/or correct seating of the closure. During the inspection, it is conceivable that the closed containers are each stopped at an inspection position that is fixed in relation to an optical 3D measuring sensor or are continuously transported onwards.

In subsequent step 102, the container together with its closure is captured at least in part by way of an optical 3D measuring method. The optical 3D measuring method can be, for example, a stereoscopic 3D measuring method in which the container together with its closure are at least in part captured from two different image perspectives. 3D data can then be obtained by triangulation from the camera images of the two different image perspectives. In the stereoscopic 3D measuring method, it is conceivable that the container together with its closure is at least in part illuminated by a diffuse or structured light source. This results in particularly high measurement dynamics with respect to the surface of the container and the closure and a simpler correlation of the same object points in the two image perspectives, respectively. Alternatively, it is also conceivable that the container together with its closure are at least in part captured by way of a light-section 3D measuring method, where they are illuminated from a first direction using a structured light source and captured with a camera from a second direction that is angled thereto. It is conceivable that the structured light source is formed by a laser or a projector for the projection of a light pattern. The perspective of the light source is blended with the image perspective of the camera and corresponding 3D data is triangulated. The resolution of the 3D data is lower than 0.5 mm, but can be even lower up to 0.1 mm or yet lower.

After performing the optical 3D measuring method, 3D data is then generated in step 103, preferably 3D points, 3D line elements and/or 3D area elements (triangles or rectangles). They are then stored in a suitable data format, for example, in an electronic memory or in a database.

Subsequently, in step 104, the 3D data of the closure and the 3D data of the container are identified and separated. The identification of the closure or of the container, respectively, can be effected by automatic masking of the 3D data or the image data, since the closure type or container type used is indeed known. It is conceivable that a reference container or reference closure, respectively, is first measured and the 3D data is associated manually thereto. Subsequently, the 3D data of the subsequently inspected containers can then be separated from their closures due to the association.

By separating the 3D data of the closure from the 3D data of the container, geometric correlation features between the closure and the container can be determined in subsequent step 105. For example, the center or another suitable reference point of the closure is determined from its 3D data. The same is performed for the container. The correct seating of the closure can then be calculated from the distance between the closure and the container. In detail, the height and the eccentricity of the closure relative to the container can be calculated. If the height or the eccentricity, respectively, fails a tolerance range, then it can be concluded that the closure is not seated correctly.

In further step 106, the 3D data of the closure is then compared with a reference geometry. The reference geometry can be a CAD dataset with construction data of the closure. Subsequently, in step 107, the face area of the closure is isolated and its curvature relative to the CAD dataset, for example, a camber, is determined. If the camber is too low, it can be concluded that there is too little curvature of the closure and thus an internal pressure in the container that is too low. Consequently, by comparing the 3D data of the closure with the reference geometry, it can be determined whether the closure is seated tightly on the container.

In step 108, it is then decided on the basis of the foregoing results whether the container is tight and the closure is seated correctly. If this is the case, then the container is supplied to further processing steps in step 109, for example, to a packaging machine. If this is not the case, then the container is excluded from further processing and ejected in step 110. It can then be, for example, recycled or cleaned.

In step 112, the next container is selected and steps 101-110 are performed for that container as described above.

Due to the fact that an optical 3D measuring method 102-103 is used in the above-described inspection method with which the container is at least in part captured together with its closure, particularly high-resolution 3D data is first generated without contact. As a result, the subsequent method steps 104-107 can each be adjusted or parameterized to the type of container or closure used, so that inspection method 100 can be used in a particularly flexible and reliable manner for different types of closures and containers. The inspection is therefore done mainly virtual in the computer and is therefore very easy to customize, without replacing hardware components.

Figure 2:
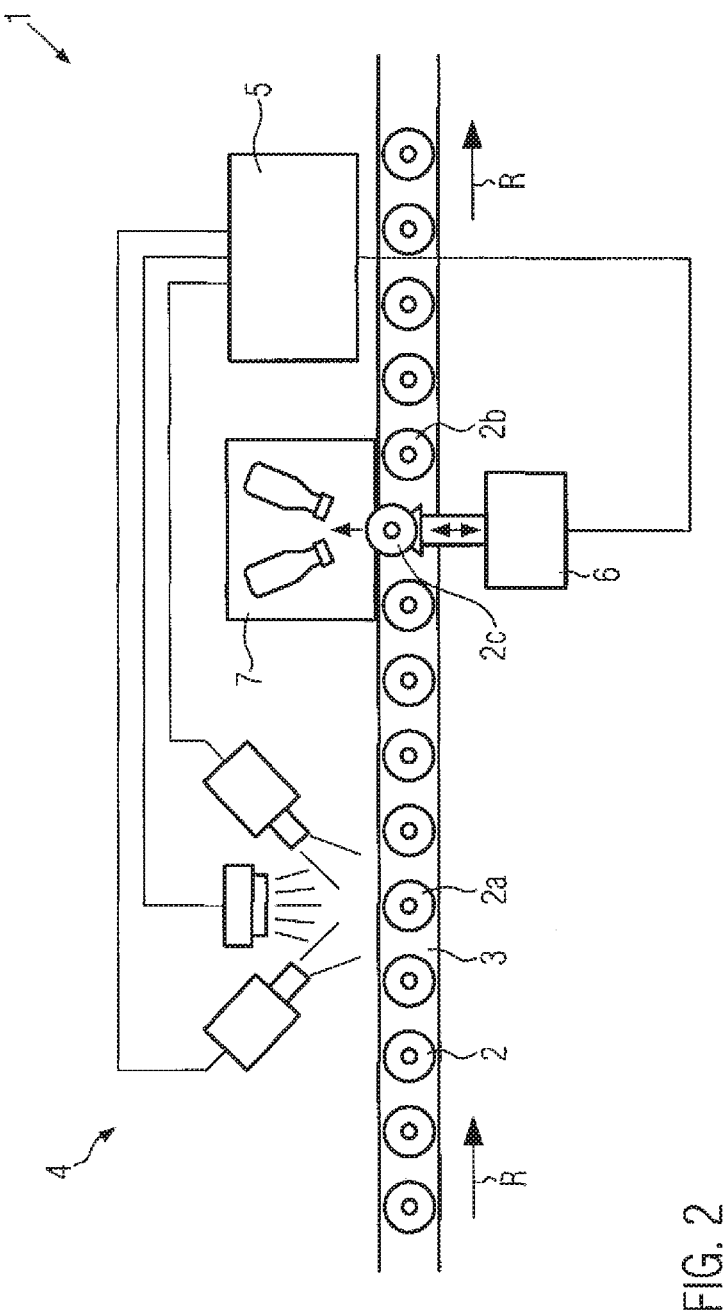
FIG. 2 shows an embodiment of an inspection device for performing the inspection method illustrated in FIG. 1.

FIG. 2 shows an embodiment of an inspection device 1 for performing inspection method 100 from FIG. 1. It can be seen that containers 2 are transported in the conveying direction R by transport apparatus 3 to optical 3D measuring sensor 4. Transport apparatus 3 is presently, for example, a conveyor belt, but any other suitable transport apparatus is also conceivable, such as a carousel. In addition, containers 2 are transported continuously along the conveying direction R so that a particularly high machine throughput is possible. Alternatively, it is also conceivable that containers 2 each stop at an inspection position.

It can also be seen that container 2a together with its closure is presently detected by optical 3D measuring sensor 4 obliquely from above from one perspective. Optical 3D measuring sensor 4 as well as optical 3D measuring method used therewith shall be described in more detail below with reference to FIG. 3.

The captured image data of 3D measuring sensor 4 is evaluated by evaluation device 5 associated therewith and 3D data of container 2a or its closure, respectively, is generated therefrom. For this purpose, evaluation device 5 is configured with a microprocessor (CPU), a memory and the necessary data interfaces. In other words, evaluation device 5 is an image processing unit with which the images captured by 3D measuring sensor 4 are evaluated. Furthermore, evaluation device 5 controls the light source of 3D measuring sensor 4 and method steps 102-108 previously described with reference to FIG. 1 are performed.

If it is now decided on the basis of method steps 102-108 that, for example, container 2c presently shown has a leak and/or the closure is not seated correctly, then it is automatically ejected by discharge device 6 from transport apparatus 3 into bin 7. In contrast, it was determined with inspection device 1 or inspection method 100, respectively, for container 2b presently shown that the closure is tight and is seated correctly. Consequently, container 2b is transported onward by transport direction [sic: apparatus] 3 in the conveying direction R, for example, to a packaging station, presently not shown.

Figure 3:
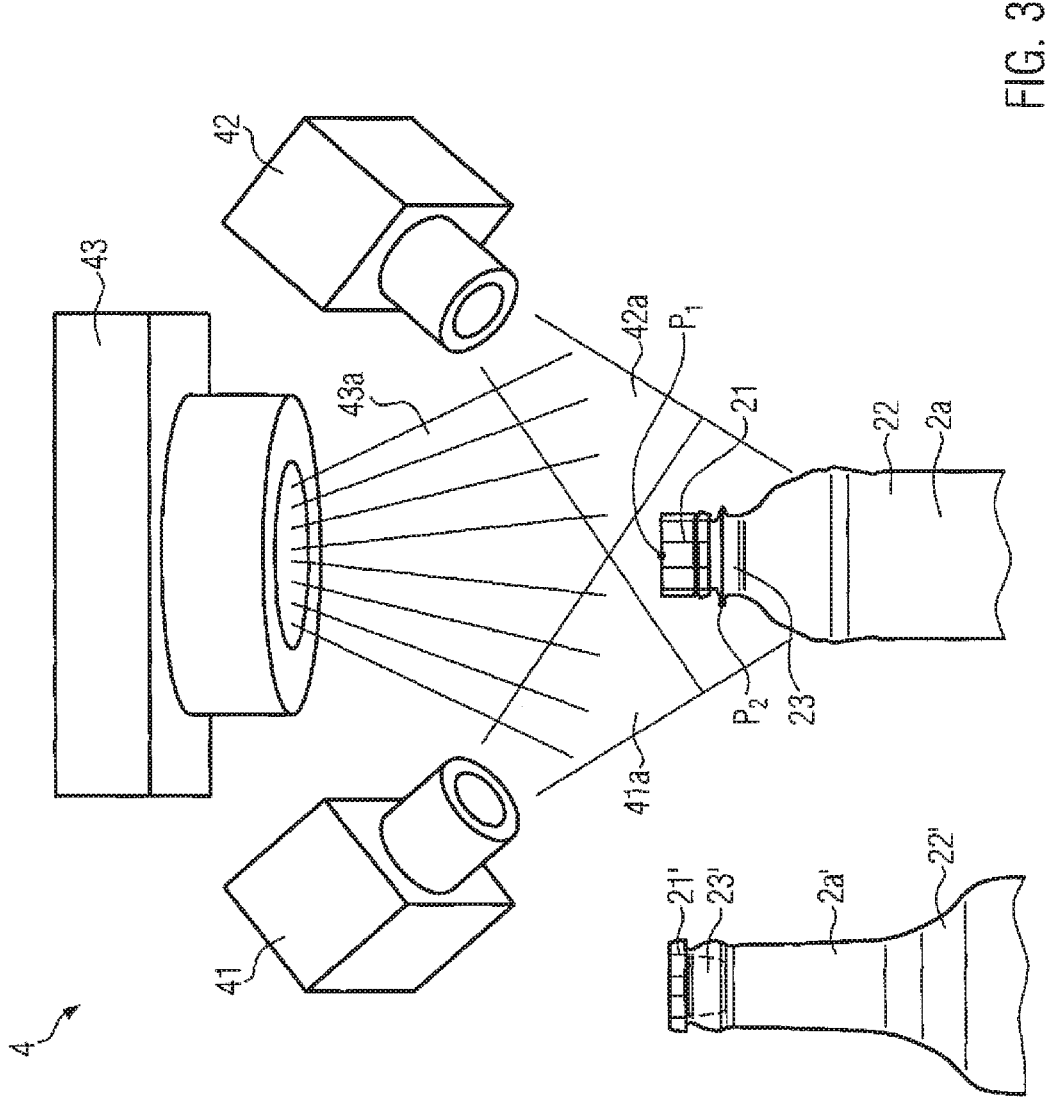
FIG. 3 shows an embodiment of the optical 3D measuring sensor illustrated in FIG. 2.

FIG. 3 shows in detail an embodiment of optical 3D measuring sensor 4 of inspection device 1 from FIG. 2. The two cameras 41 and 42 are shown, which capture container neck 23 and closure 21 of container 2a from two different image perspectives 41a, 42a. In addition, it is conceivable that container body 22 is additionally detected with a suitable measuring field. In the embodiment illustrated in FIG. 3, container 2a is a PET plastic bottle with a screw cap 21. However, a glass bottle 2a' with a crown cap 21' shown on the left-hand side in FIG. 3 can just as well be captured with 3D measuring sensor 4, so closure control can be performed reliably there as well.

Furthermore, 3D measuring sensor 4 comprises diffuse light source 43, by use of which container 2a is illuminated particularly uniformly in order to perform accurate measurement, irrespective of the nature of the surface.

The optical 3D measuring method is described in more detail based on example points $P_1$ and $P_2$: During the inspection, points $P_1$ and $P_2$ are captured by two cameras 41 and 42 from different image perspectives 41a and 42a. Due to the different image perspectives, point $P_1$ is located at different image pixels in the two camera images. By calibrating cameras 41 and 42, the exact location of point $P_1$ and its associated coordinate in space can then be calculated as a 3D point. The same applies to point $P_2$. This is therefore a stereoscopic 3D measuring method.

It is also conceivable that only one camera with a stereoscopic objective lens is used instead of the two cameras 41 and 42 and images the two different image perspectives 41a and 42a onto a single image sensor. It is also conceivable that additional cameras are used for higher measurement accuracy or automatic calibration.

Alternatively, it is also conceivable that a structured light source is used instead of diffused light source 43. With the structured light source, the object points, for example, points $P_1$ and $P_2$, can be identified more easily in the camera images of cameras 41 and 42.

Furthermore, it is alternatively conceivable that 3D measuring sensor 4 is not configured for a stereoscopic, but for a light-section 3D measuring method. In this case, container 2a or closure 21, respectively, is at least in part illuminated with a structured light source and captured only by a single camera from one image perspective. The structured light source there serves quasi as an inverse camera or as a light plane (laser for projection of a laser line).

Overall, particularly high-resolution 3D data of container 2a is therefore recorded by inspection method 100 previously described and by inspection device 1 in FIGS. 1-3, respectively. As a result, the actual closure control can take place predominantly virtually on the basis of the 3D data recorded and is then particularly easily customized to different container or closure types by way of an adaptation of the evaluation method. Therefore, reliable closure control is possible even in small spaces and without high equipment complexity.

It is understood that the features previously mentioned in the embodiments described are not restricted to these specific combinations and are also possible in any other combination.

The invention claimed is:

1. A method for closure control of a container, the method comprising:
    performing, by an inspection apparatus, optical 3D measuring of a closed container, the closed container comprising a closure coupled to the container;
    generating, by the inspection apparatus, 3D data based on the optical 3D measuring; and
    processing, by an evaluation device, the 3D data to determine at least one of tightness or correct seating of the closure relative to the container.

2. The method of claim 1, wherein the 3D data comprises 3D data of the closure and 3D data of the container, wherein the processing of the 3D data comprises separating the 3D data of the closure from the 3D data of the container.

3. The method of claim 1, wherein the processing of the 3D data further comprises determining geometric correlation features between the closure and the container.

4. The method of claim 1, wherein the processing of the 3D data further comprises determining one or more of a position, a height, a crooked seat, an eccentricity of the closure relative to the container, or a curvature of the closure.

5. The method of claim 1, wherein the processing of the 3D data further comprises:
    comparing the 3D data with a reference geometry of at least one of the closure or the container; and
    determining, based on the comparing, deformation data of the closure.

6. The method of claim 1, wherein the optical 3D measuring comprises light-section 3D measuring comprising:
    illuminating at least a portion of the container and the closure from a first direction via a structured light source; and
    capturing, by a camera, an image of the container and the closure from a second direction that is different from the first direction.

7. The method of claim 1, wherein the optical 3D measuring comprises:
    capturing, three-dimensionally with a resolution of lower than 0.5 mm, an image of at least a portion of the container and the closure.

8. The method of claim 1, wherein the optical 3D measuring comprises:
    capturing, three-dimensionally with a resolution of lower than 0.2 mm, an image of at least a portion of the container and the closure.

9. The method of claim 1, wherein the optical 3D measuring comprises:
    capturing, three-dimensionally with a resolution of lower than 0.1 mm, an image of at least a portion of the container and the closure.

10. The method of claim 1, wherein an image of at least a portion of the closure or a mouth of the container are captured by a pericentric objective lens.

11. The method of claim 1 further comprising:
    transporting, by a transport apparatus, the closed container to the inspection apparatus;
    determining whether at least one of the closed container is tight or the closure is seated correctly in relation to the container;
    in response to determining that the container is tight and the closure is seated correctly, transporting the container; and
    in response to determining that the container is not tight or the closure is not seated correctly, ejecting the container.

12. The method of claim 1, wherein the 3D data comprises one or more of 3D points, 3D line elements, or 3D area elements.

13. The method of claim 1, wherein the optical 3D measuring comprises stereoscopic 3D measuring comprising capturing images of at least a portion of the container and the closure from at least two image perspectives.

14. The method of claim 13, wherein the stereoscopic 3D measuring comprises illuminating one or more portions of the container and the closure by a diffused light source.

15. The method of claim 13, wherein the stereoscopic 3D measuring comprises illuminating one or more portions of the container and the closure by a structured light source for correlation of object points in the at least two image perspectives.

16. An inspection device for closure control of containers, the inspection device comprising:
    a transport apparatus to transport a closed container comprising a closure coupled to a container;
    an optical 3D measuring sensor to capture a three-dimensional (3D) image of at least a portion of the container and the closure; and
    an evaluation device to process the 3D image to determine at least one of tightness or correct seating of the closure relative to the container.

17. The inspection device of claim 16, wherein the optical 3D measuring sensor is to perform stereoscopic 3D measuring of the closed container, wherein the optical 3D measuring sensor comprises a camera comprising a stereoscopic objective lens, wherein the optical 3D measuring sensor is coupled to a diffused or structured light source.

18. The inspection device of claim 16, wherein the optical 3D measuring sensor is to perform stereoscopic 3D measuring of the closed container, wherein the optical 3D measuring sensor comprises two or more cameras, each of the two or more cameras comprising an objective lens, wherein the optical 3D measuring sensor is coupled to a diffused or structured light source.

19. The inspection device of claim 16, wherein the optical 3D measuring sensor is to perform light-section 3D measuring of the closed container, wherein the optical 3D measuring sensor comprises at least one camera comprising an objective lens coupled to a structured light source.

20. The inspection device of claim 18, wherein the objective lens is pericentric.

* * * * *